(12) United States Patent
Jaramaz et al.

(10) Patent No.: US 9,211,163 B1
(45) Date of Patent: Dec. 15, 2015

(54) APPARATUS AND METHOD FOR MINIMALLY INVASIVE INTRACRANIAL HEMATOMA EVACUATION WITH REAL-TIME ASSESSMENT OF CLOT REDUCTION

(76) Inventors: Branislav Jaramaz, Pittsburgh, PA (US); Michael Y. Oh, Pittsburgh, PA (US)

( * ) Notice: Subject to any disclaimer, the term of this patent is extended or adjusted under 35 U.S.C. 154(b) by 803 days.

(21) Appl. No.: 12/912,658

(22) Filed: Oct. 26, 2010

(51) Int. Cl.
 *A61B 19/00* (2006.01)
 *G01R 33/28* (2006.01)
 *A61B 5/06* (2006.01)

(52) U.S. Cl.
 CPC .......... *A61B 19/5244* (2013.01); *G01R 33/285* (2013.01); *A61B 5/06* (2013.01)

(58) Field of Classification Search
 USPC .......................................... 600/466; 606/180
 See application file for complete search history.

(56) References Cited

U.S. PATENT DOCUMENTS

| | | | |
|---|---|---|---|
| 5,419,774 A * | 5/1995 | Willard et al. | 604/22 |
| 5,779,713 A * | 7/1998 | Turjanski et al. | 606/108 |
| 5,787,886 A | 8/1998 | Kelly et al. | |
| 5,823,990 A | 10/1998 | Henley | |
| 6,076,008 A | 6/2000 | Bucholz | |
| 6,083,237 A | 7/2000 | Huitema et al. | |
| 6,626,890 B2 | 9/2003 | Nguyen | |
| 6,673,023 B2 | 1/2004 | Pflueger | |
| 6,773,402 B2 | 8/2004 | Govari | |
| 7,008,381 B2 | 3/2006 | Janssens | |
| 7,018,354 B2 | 3/2006 | Tazi | |
| 2005/0228417 A1 * | 10/2005 | Teitelbaum et al. | 606/159 |
| 2007/0083100 A1 | 4/2007 | Schulz-Stubner | |
| 2008/0140104 A1 * | 6/2008 | Bender et al. | 606/170 |
| 2010/0114017 A1 * | 5/2010 | Lenker et al. | 604/96.01 |
| 2010/0249817 A1 * | 9/2010 | Mark | 606/170 |
| 2011/0261180 A1 * | 10/2011 | Simon et al. | 348/77 |

FOREIGN PATENT DOCUMENTS

| | | |
|---|---|---|
| CN | 2642318 | 7/2005 |
| CN | 2740140 | 11/2005 |
| CN | 2848138 | 12/2006 |

OTHER PUBLICATIONS

Nagasaka et. al., Balanced Irrigation-Suction Technique with a Multifunctional Suction Cannula and . . . , Neurosurgery, Oct. 2009, E826, vol. 65, Congress of Neurological Surg.

* cited by examiner

*Primary Examiner* — Unsu Jung
*Assistant Examiner* — Daniel Huntley
(74) *Attorney, Agent, or Firm* — The Ronald Law Group, LLC

(57) ABSTRACT

Method and apparatus for the evacuation of intracerebral hematomas comprises a minimally invasive non-operating room surgical apparatus within a neuro-navigation system that can provide real-time imaging of the ICH evacuation procedure. Apparatus uses an auger housed within an apertured lumen which, when placed in proximity to a hematoma and rotated in an appropriate direction, causes the removal of the clotty material from the hematoma. Apparatus also includes ultrasonic imaging capability and an electromagnetic tracking coil to enable real-time, three-dimensional visualization of the evacuation procedure.

6 Claims, 4 Drawing Sheets

APPARATUS AND METHOD FOR MINIMALLY INVASIVE INTRACRANIAL HEMATOMA EVACUATION WITH REAL-TIME ASSESSMENT OF CLOT REDUCTION

FIELD OF THE INVENTION

This invention relates generally to the field of minimally invasive surgery and, more particularly, to the removal of life-threatening clots from brain tissue.

BACKGROUND OF THE INVENTION

Generally, the human skull can be thought of as a fixed volume container. As such, any increase in the volume of the contents of the skull necessarily results in an increase in intracranial pressure (ICP). While there is some normal variation in ICP on a daily basis, elevated ICP beyond the normal range can have substantial adverse effects on the health of an individual. These adverse affects can include loss of consciousness, paralysis, coma, difficulty breathing, and death.

There are many causes of elevated ICP, but the focus of the present application is on intracranial hematomas, which can occur when a vessel in the brain is torn and bleeds. This can occur, for example, as a result of causes as varied as a blow to the head or weakened arterial walls due to an extensive period of hypertension. As used herein, hematomas are defined as abnormal localized collections of blood where the blood is usually at least partially clotted and located inside a bodily organ. Thus, when the brain bleeds, the blood forms clots and is referred to as an intracranial hematoma. Notably, these types of hematomas are dangerous not only because they cause an increase in ICP, but also because they have the capability of shifting the location of other parts of the brain, which can have additional adverse effects on the brain stem.

There are three main kinds of intracranial hematomas: epidural, subdural and intracerebral. While all three types can be deadly if untreated, both epidural and subdural hematomas, also called extra-axial hematomas, occur near the outer part of the brain, close to the skull, and can be treated by creating a burr hole or removing a portion of the skull to relieve the pressure and deal with the hematoma directly. Intracerebral hematomas (ICH), however, occur within the brain tissue itself and are much more difficult to treat with surgical intervention because they are hard to access without causing additional damage to surrounding brain tissue. Improving patient outcomes is an urgent concern. Approximately twenty thousand Americans die each year due to ICH-related problems and this number is expected to double in the next fifty years.

There are two main treatments: medication and surgery. Medical management usually involves controlling blood pressure and reversing the effects of any anti-coagulants in the patient's system in the hopes that the situation can be resolved in a conservative way. Sometimes, however, whether due to the location, cause, volume of the bleed, or development of edema around the blood clot, surgical intervention is recommended.

Presently used surgical techniques include craniotomy, stereotactic-guided evacuation, endoscopic evacuation, and catheter evacuation, but each has their problems. The craniotomy procedure involves removing a portion of the skull so that pressure is relieved and the hematoma can be removed, but it must be performed in a sterile operating room and is likely to induce further trauma to the brain. Stereotactic-guided evacuation is less invasive than a craniotomy, but requires an enormous amount of equipment, time and cost for a procedure that is ultimately less effective than a craniotomy at reducing the size of the hematoma. Endoscopic evacuation is not well-known to neurosurgeons, is not well-suited to emergency situations and still requires the use of an operating room and general anesthesia. Finally, current catheter-based approaches can be performed in the ICU instead of the OR, but necessitate the use of blood thinners and result in slower than desired drainage of the hematoma. Additionally, repeated catheter placements can cause additional damage to other parts of the brain. None of these existing surgical techniques is particularly well-suited to the treatment and remediation of an ICH.

In view of the foregoing, a need has been recognized in connection with improving upon existing tools and techniques for minimally invasive ICH evaluation and evacuation in a less disruptive and quicker way that does not involve general anesthesia or the use of an operating room.

A need has also been identified for new surgical tools and techniques that maximize the amount of hematoma that is removed while minimizing the damage to surrounding tissue. Additionally, it would be preferable for health care providers to use these new surgical tools and techniques in the ICU instead of the OR due to the approximately three additional hours a typical patient would be required to wait prior to intervention in an operating room setting. With elevated ICP, time is the enemy. Quicker intervention will lead to better patient outcomes.

For a better understanding of the present invention, together with other and further features and advantages thereof, reference is made to the following description, taken in conjunction with the accompanying drawings, and the scope of the invention that will be pointed out in the appended claims.

SUMMARY OF THE INVENTION

It is an object of some aspects of the present invention to provide improved apparatus and methods for minimally invasive intracerebral hematoma evaluation and evacuation with real time, three-dimensional imaging of the procedure. It is a further object to enable hematoma evaluation and evacuation in a non-operating room setting to enable quicker intervention, better outcomes and reduced heath care cost.

In preferred embodiments of the present invention, the apparatus comprises an elongated, generally circular body with a proximal portion, distal portion, outer wall and a longitudinal axis. A lumen is formed inside the body and extends from the proximal portion to the distal portion. The lumen houses an auger that is rotatably disposed therein and has one or a plurality of blades located near the distal portion. In the area of the blades, an aperture is formed in the body, which permits fluid movement from outside the body into the lumen when the auger is rotated. It is also contemplated that a vacuum port can be disposed on the proximal portion of the lumen to provide gentle suction to assist the auger with removal of the hematoma material. In the preferred embodiment, an ultrasound catheter is disposed at the distal portion of the body and is adapted to capture images of the hematoma material prior to and during the evacuation procedure. Further, an electromagnetic tracking coil is also disposed at the distal portion of the body and is adapted to track the location of the apparatus within the patient's brain when data from the coil is mapped onto a previously taken CT scan. Additionally, a cannula is also formed within the body and provides access to the distal portion of the apparatus to enable injection of saline or a therapeutic agent into the hematoma material.

The invention also comprises a method of removing hematoma material from a patient's brain comprising inserting the previously discussed apparatus into the brain along a previously determined pathway and confirming with ultrasound and electromagnetic or optical device tracking that the distal portion of the apparatus is placed in the vicinity of the clot. Once the apparatus is properly placed, as confirmed by visualization using the discussed technologies, the hematoma material is removed with the use of an auger and, possibly, with the assistance of gentle suction. The next step is to use the ultrasound catheter to verify the amount of the clotty material has been removed.

Other objects and features of the invention will be pointed out and apparent to those skilled in the art hereafter.

DESCRIPTION OF THE PREFERRED EMBODIMENTS

The present invention provides an improved method and apparatus for the evacuation of intracerebral hematomas. More specifically, an aspect of the present invention is a minimally invasive surgical apparatus within a neuro-navigation system that can provide real-time imaging of the ICH evacuation procedure, including the clot itself. The principal mechanism by which the hematomas are evacuated is an Archimedes screw or auger, which is housed within an apertured lumen and, when placed inside a hematoma and rotated in an appropriate direction, causes the removal of the clotty material. The apparatus also includes ultrasonic imaging capability so that the surgeon can monitor its placement and the evacuation progress in real time. Additionally, an aspect of the invention is that, in a preferred embodiment, the distal portion of the apparatus can house an electromagnetic tracking coil so that the surgeon can use it with a navigation system.

The Probe

Figure 1:
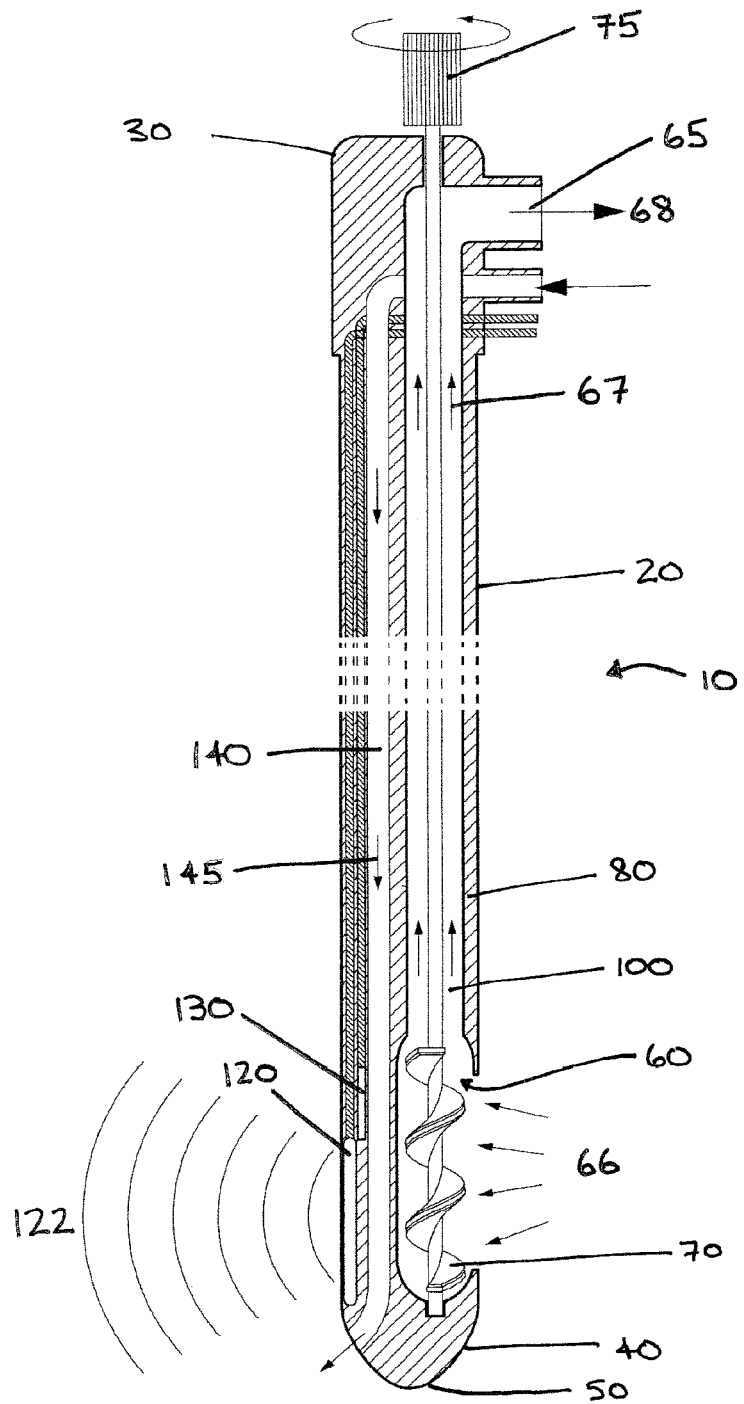
FIG. 1 is a schematic view of the hematoma evacuation catheter of the present invention.

Referring now to FIG. 1, a preferred embodiment of the probe 10 of the present invention includes an elongated body 20, generally circular in cross-section, having a proximal portion 30 and a distal portion 40. The body 20 is designed to have a small diameter, approximately 6.5 mm, in order to allow insertion through a burr hole in the patient's skull, which is typically 12 mm in diameter, under local anesthetic in the ICU. The length of the probe 10 in the elongated dimension is shorter than some other minimally invasive devices due to the fact that the typical hematoma size is 2.5 to 3 cm at depths of from 3 to 7 cm within the brain. Thus, the elongated dimension length of the probe 10 in a preferred embodiment is approximately 20 cm. The distal portion 40 of the body 20 has a blunted or rounded tip 50 to minimize damage to brain tissue during insertion. Immediately adjacent to the tip 50, the body 20 is cut away to form an aperture 60, which exposes an auger blade 70 rotatably housed within an auger lumen 100 axially disposed within the body 20 adjacent to an outer wall 80 in order to facilitate uptake of clotty material when in use. The auger lumen 100 extends along the longitudinal axis of the body 20 from the aperture 60 to the proximal portion 30 where an exhaust port 65 is formed in the body 20. In a preferred embodiment, clotty material from the hematoma is drawn into the auger lumen 100 via the rotational action of the auger blade 70 created by the physician by twisting the auger handle 75 as is illustrated by arrows 66. The clotty material is then pushed up the auger lumen 100, as illustrated by arrows 67, by additional clotty material being drawn in at the aperture 60 by the rotational motion of the auger 70 and it is ultimately expelled from the auger lumen 100 at the exhaust port 65. In an alternative embodiment, a vacuum suction 68 is gently applied to the exhaust port 65 to facilitate removal of the clotty material.

An ultrasound catheter 120 is disposed in the outer wall 80 of the distal portion 40 of the body 20 at a location generally opposite the aperture 60 of the auger lumen 100. In a preferred embodiment, the ultrasound catheter 120 has an outside diameter of approximately 2.65 mm (such as the ACUSON AcuNav catheter by Siemens Medical Systems, Inc.). This ultrasound catheter 120 is housed in the distal portion 40 near the tip 50 so that it may be used to acquire images of brain tissue and hematoma material during a procedure. Curved lines 122 demonstrate the location of the imaging that can be performed using the ultrasound catheter 120.

To the extent that saline is required at the imaging site in order to facilitate ultrasound imaging, a preferred embodiment provides an approximately 1.5 mm diameter cannula 140 that is axially disposed within the body 20 through which saline may be delivered to the imaging location at the distal portion 40 generally adjacent the blunt tip 50. Additionally, the cannula 140 can also be used as a convenient channel for the delivery of thrombolytic or other therapeutic agents to the clot and surrounding brain tissue, as illustrated by arrows 145.

In still another embodiment, an electromagnetic tracking coil 130, such as the miniature sensor coil manufactured by Northern Digital Inc., is disposed in the distal portion 40 of the body 20 a known distance from the tip 50. This coil 130 is approximately 0.9 mm in diameter and will permit not only tracking of the probe 10 via a navigation system (such as Aurora by Northern Digital, Inc.), but also three-dimensional reconstruction of ultrasound data collected by the ultrasound catheter 120 by either segmenting out the hematoma contour in each image and then assembling the contours in a three-dimensional shape using their relative positions gleaned from the tracking data or populating a three-dimensional raster space with intensity information from each ultrasound image. In this manner, it is possible to obtain a real-time, three-dimensional assessment of hematoma location, size, and intra-procedure reduction.

Figure 2:
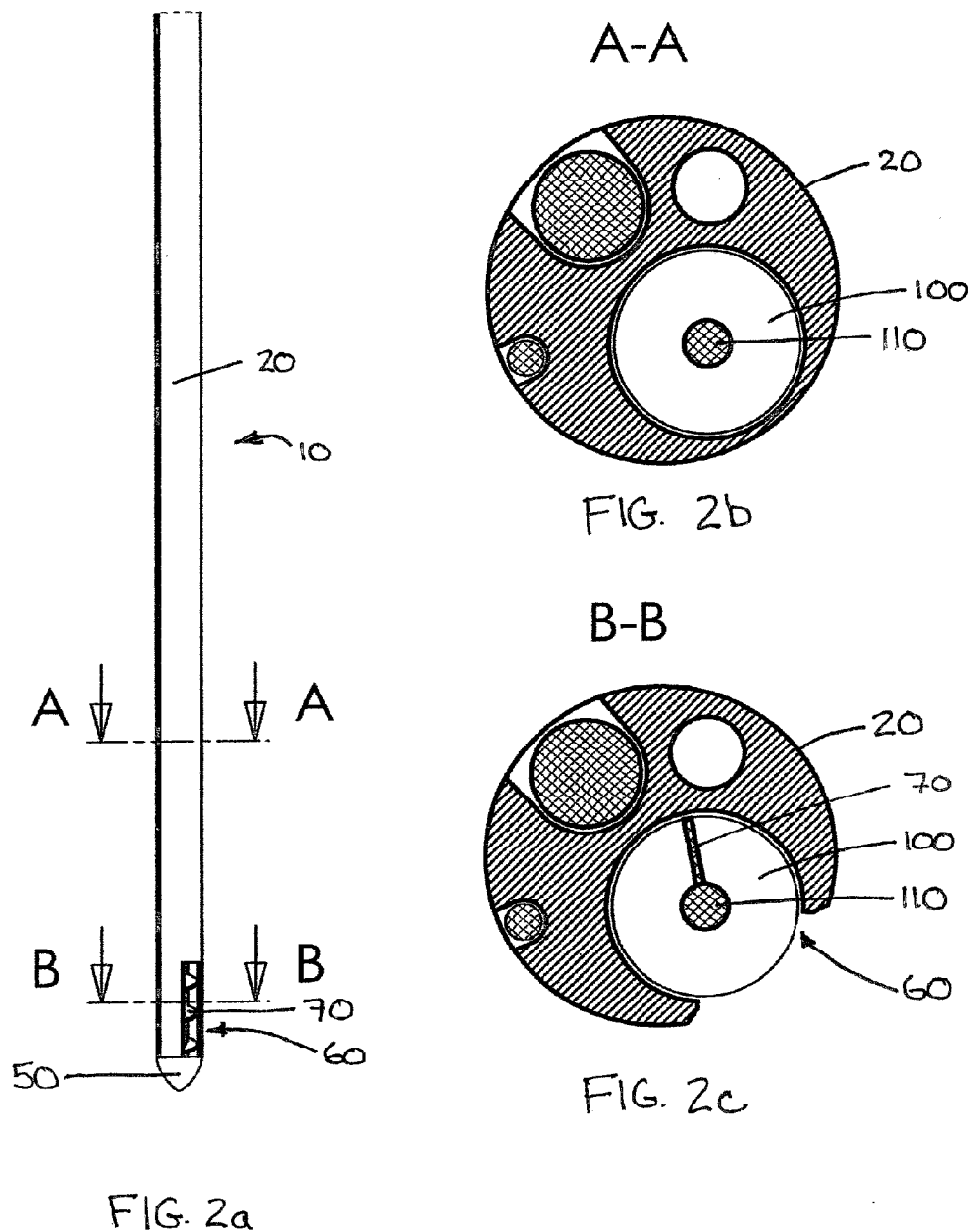
FIG. 2a is a side elevational view of the hematoma evacuation catheter of the present invention.
FIG. 2b is a cross-sectional view of the catheter of FIG. 2a along segment A-A.
FIG. 2c is a cross-sectional view of the catheter of FIG. 2a along segment B-B.

Referring now to FIG. 2a, a side elevational view of the probe 10 is shown. The aperture 60 and auger blade 70 are seen near the tip 50.

FIGS. 2b and 2c are cross-sectional views along segments A-A and B-B of FIG. 2a respectively, illustrating the generally circular cross-sectional shape of the body 20. In a preferred embodiment, the body 20 is manufactured from substantially rigid materials that are known not to disrupt electromagnetic fields and comprises a lumen 100, which houses an auger 110. While an example of such a substantially rigid material is polyether ether ketone (PEEK), other materials will be well-known to those skilled in the art.

In a further preferred embodiment, the auger 110 has a blade 70 having a largest diameter of 3 mm near the blunt tip 50, said diameter of the blade 70 diminishing as the axial distance from the tip 50 increases in order to increase the efficiency with which the clotty material is removed through the aperture 60 when the auger 110 is rotated. In an alternative embodiment, a gentle vacuum may be applied across the auger 110 in order to assist in the removal of any clot material. In a further alternative embodiment, the auger 110 may comprise more than one blade.

Method of Use of Probe

Figure 3:
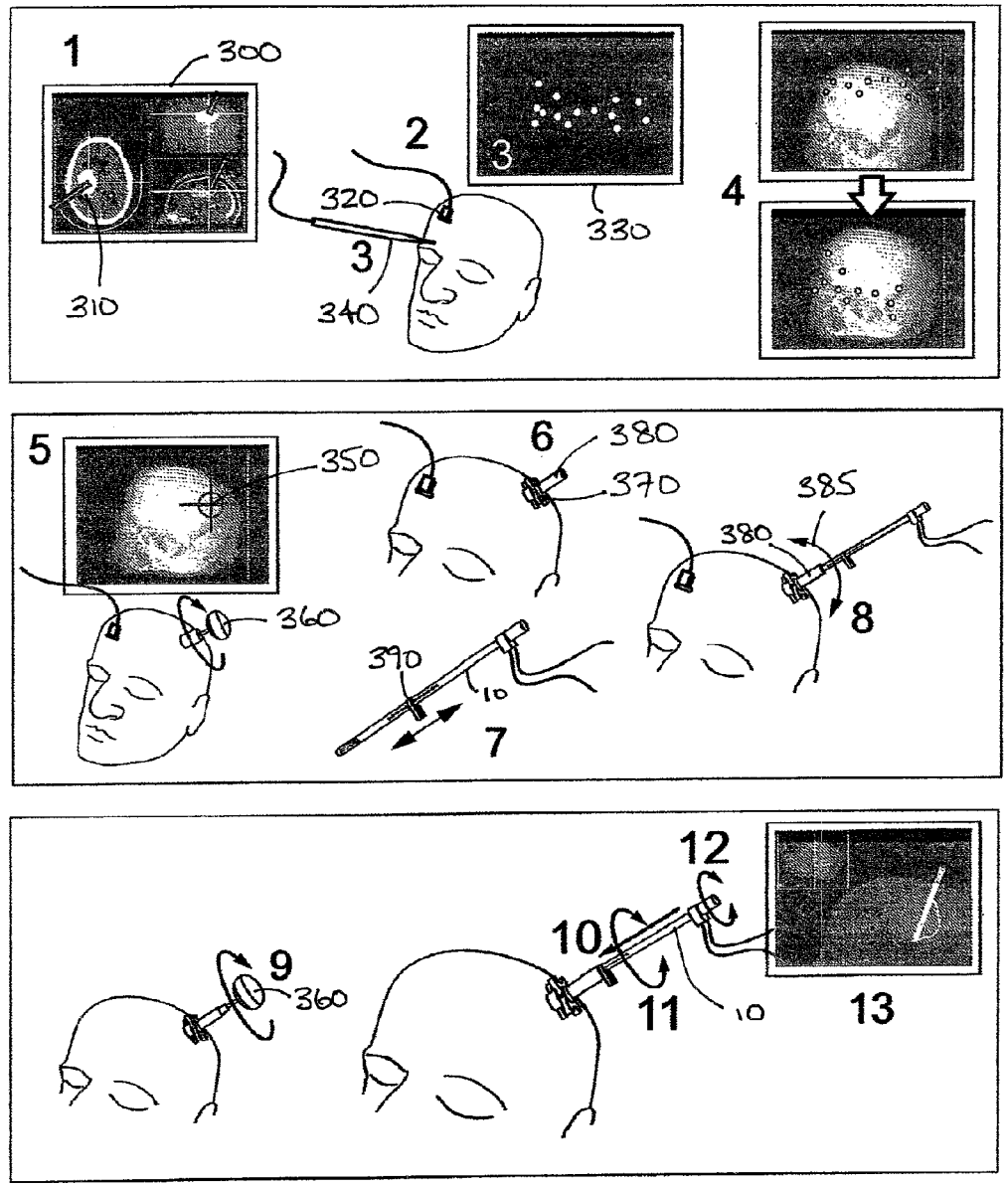
FIG. 3 is a schematic flow chart illustrating the preferred method of use of the catheter of the present invention.

By way of illustration of the method of use of the probe of the present invention, reference is now made to FIG. 3, which schematically demonstrates the intended manner of use of a preferred embodiment of the present invention.

Upon arrival at a hospital or other treatment facility, a patient exhibiting symptoms consistent with ICH is given a CT scan and the resulting CT image 300 reveals a hematoma 310. Then, an electromagnetic or optical tracking sensor 320 is attached to the patient's skull for reference purposes and skull surface points 330 are collected using a tracked point probe 340 as is well known in the art. The skull surface points 330 are then registered to the CT image 300 and the optimal path providing safe access to the hematoma is identified and an entry point 350 is located with the point probe 340 and identified.

Next, a twist drill trephine 360, or similar device as is known in the art, is used to create a partial thickness burr hole (not shown) in the patient's skull, having an approximate diameter of 12 mm, at the entry point 350 and a bottom ring 370 of a trajectory guide is screwed into the burr hole. Then, a guide tube 380 is attached to the ring 370 and a depth gauge 390 is set on the probe 10 so that it is not inserted into the patient's brain further than medically needed. Using navigation feedback, the correct trajectory of the guide tube 380 is then selected, as demonstrated by arrows 385 and locked in place. Then, the burr hole is completed using the twist drill trephine 360 and the probe 10 is inserted into the brain through the guide tube 380 until it reaches the predetermined position. Using the combination of the feedback from the electromagnetic tracking sensor 320, the tracking coil 130 in the probe 10, and the ultrasound images taken by the ultrasound catheter 120 mapped to the CT scan, the system of the present invention is able to provide real-time three-dimensional information about the location of the probe, the extent of the hematoma and the progress of the evacuation of the hematoma.

Figure 4:
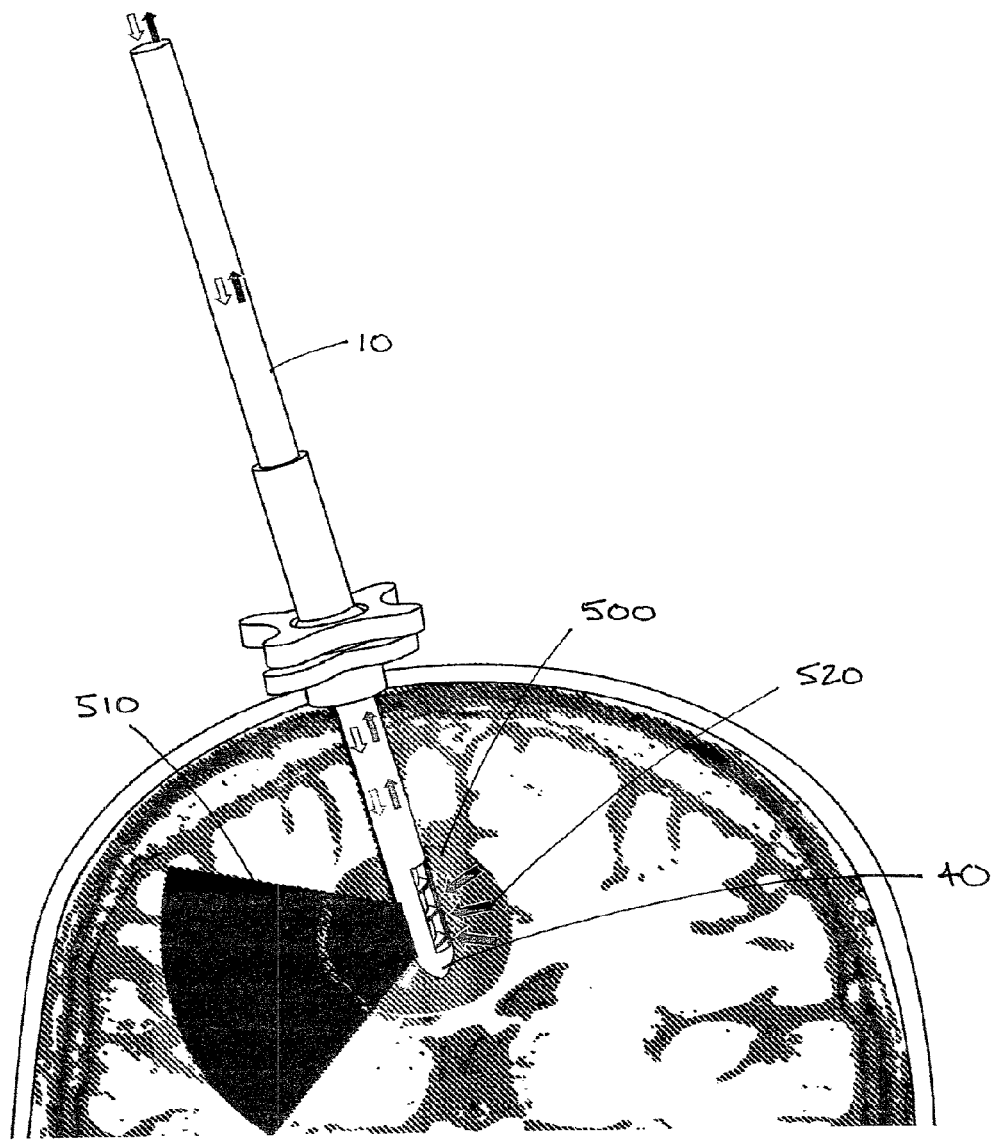
FIG. 4 is a perspective view of the catheter of the present invention positioned in a brain.

Referring now to FIG. 4, once the probe 10 is in place with the distal portion 40 within the hematoma 500, the probe 10 is spun 180 degrees in each direction to obtain a full 360 degree ultrasound view of the hematoma 500. Collection of ultrasound data is represented by the triangular darkened area 510. The ultrasound data is then compared to the previously taken CT scan and if the location is correct, the auger 110 is turned on or, in an alternative embodiment, manually twisted, and the probe 10 is gently rotated within a 360 degree range to achieve uniform evacuation, which is demonstrated by arrows 520 of the hematoma 500 and to update the ultrasound images post scan. Optionally, therapeutic or thrombolytic agents 530 can be delivered directly to the hematoma 500 or surrounding parenchyma.

If not otherwise stated herein, it is to be assumed that all patents, patent applications, patent publications and other publications (including web-based publications) mentioned and cited herein are hereby fully incorporated by reference herein as if set forth in their entirety herein.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention. Accordingly, the drawings and description are to be regarded as illustrative in nature, and not as restrictive.

What is claimed is:

1. A method of removing hematoma material from the brain of a patient who has had an intracerebral hemorrhage comprising the following steps:
   inserting an apparatus into the brain of a patient with a hematoma, the apparatus comprising an elongated rigid body having a proximal portion, a distal portion, an outer wall, and a longitudinal axis; a lumen formed within the body extending from the proximal portion to the distal portion; an auger rotatably disposed within said lumen; said auger having an auger blade disposed within the lumen at the distal portion; an aperture formed in the outer wall of the elongated body adjacent to the auger blade, said aperture in fluid communication with the lumen; whereby rotation of the auger creates suction to draw unattached hematoma material through the aperture and into the lumen, toward an exhaust port at a proximal portion of the elongated rigid body, where the unattached hematoma material can be expelled from the body; an ultrasound catheter disposed at the distal portion of the body adapted to capture images of the hematoma material during the procedure; and an electromagnetic tracking coil disposed at the distal portion of the body adapted to tracking the location of the apparatus within the patient's brain;
   tracking the distal end of the apparatus to obtain relative location data and mapping said data to a CT scan of the hematoma material;
   confirming that the distal portion of the apparatus is positioned inside the hematoma material by rotating the apparatus axially while collecting ultrasound images of the hematoma and brain tissue and mapping the images onto the CT scan in order to permit real-time, three-dimensional observation of the location of the apparatus in the patient's brain in relation to the location of the hematoma material and the effect on the surrounding brain tissue occasioned by the removal of hematoma material;
   removing the hematoma material from the brain solely by suction created by rotating the auger;
   and verifying the extent of hematoma material removed.

2. The method of claim 1, wherein the step of verifying the removal of hematoma material further comprises injecting saline through the catheter to assist with ultrasonic imaging.

3. The method of claim 1, wherein the step of removing the hematoma material from the brain further comprises rotating the apparatus about its longitudinal axis within a 360 degree range while optionally simultaneously rotating the auger to achieve complete evacuation of the hematoma material.

4. The method of claim 3, wherein the step of removing the hematoma material from the brain further comprises applying vacuum suction to the lumen.

5. The method of claim 1, wherein the step of removing the hematoma material from the brain further comprises injecting a thrombolytic into the hematoma material.

6. The method of claim 1, wherein the step of verifying that all of the hematoma material has been removed further comprises rotating the apparatus about its longitudinal axis within a 360 degree range while simultaneously obtaining images with the ultrasound catheter.

* * * * *